United States Patent
Aono et al.

(10) Patent No.: US 7,833,154 B2
(45) Date of Patent: Nov. 16, 2010

(54) AUTOCLAVE STERILIZATION-COMPATIBLE ENDOSCOPE

(75) Inventors: Susumu Aono, Hachioji (JP); Toshiyuki Nihei, Hachioji (JP); Jun Matsumoto, Hino (JP); Ichiro Kagawa, Hachioji (JP); Hiroshi Endo, Hachioji (JP)

(73) Assignee: Olympus Corporation, Tokyo (JP)

( * ) Notice: Subject to any disclaimer, the term of this patent is extended or adjusted under 35 U.S.C. 154(b) by 1292 days.

(21) Appl. No.: 11/122,574

(22) Filed: May 5, 2005

(65) Prior Publication Data

US 2005/0209508 A1     Sep. 22, 2005

Related U.S. Application Data

(63) Continuation of application No. PCT/JP03/14640, filed on Nov. 18, 2003.

(30) Foreign Application Priority Data

Nov. 18, 2002    (JP)    ............... 2002-334266

(51) Int. Cl.
    *A61B 1/005*    (2006.01)
(52) U.S. Cl. .................. 600/140; 600/139; 600/141
(58) Field of Classification Search ........... 600/101, 600/118, 121–125, 138–142, 144, 146, 149; 604/523–527
    See application file for complete search history.

(56) References Cited

U.S. PATENT DOCUMENTS

| | | | |
|---|---|---|---|
| 3,746,003 A * | 7/1973 | Blake et al. ............ | 604/102.02 |
| 4,347,837 A * | 9/1982 | Hosono ................... | 600/139 |
| 4,807,598 A | 2/1989 | Hasegawa | |
| 4,841,952 A * | 6/1989 | Sato et al. .............. | 600/129 |
| 4,879,991 A * | 11/1989 | Ogiu ....................... | 600/129 |
| 5,100,386 A * | 3/1992 | Inoue ...................... | 604/103 |
| 5,110,645 A | 5/1992 | Matsumoto et al. | |
| 5,275,152 A * | 1/1994 | Krauter et al. .......... | 600/129 |
| 5,591,120 A * | 1/1997 | Machida et al. ......... | 600/140 |
| 5,620,001 A * | 4/1997 | Byrd et al. ............... | 606/202 |
| 5,695,448 A * | 12/1997 | Kimura et al. .......... | 600/121 |

(Continued)

FOREIGN PATENT DOCUMENTS

EP     0 535 847     4/1993

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An endoscope is provided with a bending tube including sequentially connected plural bending pieces constituting a bending section which is provided in a slim and elongated insertion portion and which is brought into a bending operation by remote control, a distal end section which is provided in the front end side of this bending tube and which constitutes the front end side of the insertion portion, a flexible tube section which is provided in the base end side of the bending tube and which constitutes the rear end side of the insertion portion, and a covering member which is disposed to cover the bending tube and which has elasticity in order that both end portions of the covering member are fixed to the distal end section or the flexible tube section by being fastened radially inward, wherein the relationship represented by $0.3D<d<1.0D$ is established between a thickness d of the covering member fixed by fastening and the thickness D of the covering member before being fixed by fastening.

13 Claims, 6 Drawing Sheets

U.S. PATENT DOCUMENTS

| | | | |
|---|---|---|---|
| 6,447,445 B1 * | 9/2002 | Hirano | 600/129 |
| 6,477,423 B1 * | 11/2002 | Jenkins | 607/40 |
| 6,527,748 B1 * | 3/2003 | Suzuki | 604/171 |
| 7,060,026 B2 * | 6/2006 | Ishibiki | 600/133 |
| 2001/0029317 A1 | 10/2001 | Hayakawa | |
| 2002/0010386 A1 * | 1/2002 | Matsushita et al. | 600/140 |
| 2002/0115983 A1 * | 8/2002 | Sekino et al. | 604/528 |
| 2002/0143237 A1 * | 10/2002 | Oneda et al. | 600/116 |

FOREIGN PATENT DOCUMENTS

| | | |
|---|---|---|
| JP | 63-14806 | 4/1988 |
| JP | 8-243072 | 9/1996 |
| JP | 10-99263 | 4/1998 |
| JP | 10099263 A * | 4/1998 |
| JP | 10-262905 | 10/1998 |
| JP | 2002-125916 | 5/2002 |

* cited by examiner

AUTOCLAVE STERILIZATION-COMPATIBLE ENDOSCOPE

CROSS REFERENCE TO RELATED APPLICATION

This application is a continuation application of PCT/JP03/14640 filed on Nov. 18, 2003 and claims the benefit of Japanese Application No. 2002-334266 filed in Japan on Nov. 18, 2002, the entire contents of each of which are incorporated herein by their reference.

BACKGROUND OF THE INVENTION

1. Field of the Invention

The present invention relates to an autoclave sterilization-compatible endoscope, in which a bending section is connected to a base end side of a distal end including an objective optical system.

2. Description of the Related Art

Diagnoses and treatments in body cavities are previously carried out by the use of endoscopes including bending sections in insertion portions. The bending section of the endoscope is composed of sequentially connected plural bending pieces. In order to bring the bending section including these sequentially connected bending pieces into a bending operation, a plurality of bending wires corresponding to bending directions are included in the insertion portion. Consequently, the bending section is brought into a bending operation in, for example, an upward direction by a back-and-forth movement of the bending wire.

The outer perimeter portion of the bending tube including the plural bending pieces constituting the bending section is covered with bending rubber. Both end portions of this bending rubber are fixed with respective thread-wrapped parts. The bending rubber is crushed radially inward by these thread-wrapped fixing parts. Consequently, the inner perimeter surface of the bending rubber is brought into intimate contact with the outer perimeter surface of the bending tube, so as to be fixed watertight. The thread-wrapped fixing part is fixed by adhesion with an adhesive. In this manner, the thread constituting the thread-wrapped part is prevented from untying.

SUMMARY OF THE INVENTION

An endoscope of the present invention is provided with a bending tube including sequentially connected plural bending pieces constituting a bending section which is provided in a slim and elongated insertion portion and which is brought into a bending operation by remote control; a distal end section which is provided in the front end side of this bending tube and which constitutes the front end side of the insertion portion; a tube section which is provided in the base end side of the bending tube and which constitutes the rear end side of the insertion portion; and a covering member which is disposed to cover the bending tube and which has elasticity in order that both end portions of the covering member are fixed to the distal end section or the tube section by being fastened radially inward, wherein the relationship represented by $0.3D<d<1.0D$ is established between a thickness d of the covering member fixed by fastening and the thickness D of the covering member before being fixed by fastening. In this manner, the bending rubber is prevented from interfering the bending operation of the bending section and, in addition, entrance of water into the interior of the endoscope is prevented. Furthermore, when the endoscope is put in an autoclave apparatus, entrance of large amount of high-temperature and high-pressure steam into the interior of the endoscope is prevented.

BRIEF DESCRIPTION OF THE DRAWINGS

FIG. 1 is an explanatory diagram showing the external structure of an endoscope;

FIG. 2 is a sectional view of an insertion portion of an endoscope;

FIG. 3 is a sectional view showing the junction between the front end side of a bending section and a front end cover;

FIG. 4 is a sectional view showing the junction between the base end side of the bending section and a joint tube;

FIG. 6 is a sectional view of an insertion portion of an endoscope;

FIG. 7 is a sectional view showing the junction between the front end side of a bending section and a front end cover; and FIG. 8 is a sectional view showing the junction between the base end side of the bending section and a joint tube.

DESCRIPTION OF THE PREFERRED EMBODIMENTS

The present invention will be described in detail with reference to the attached drawings.

The first embodiment of the present invention will be described with reference to FIG. 1 to FIG. 4.

(Construction)

Figure 1:
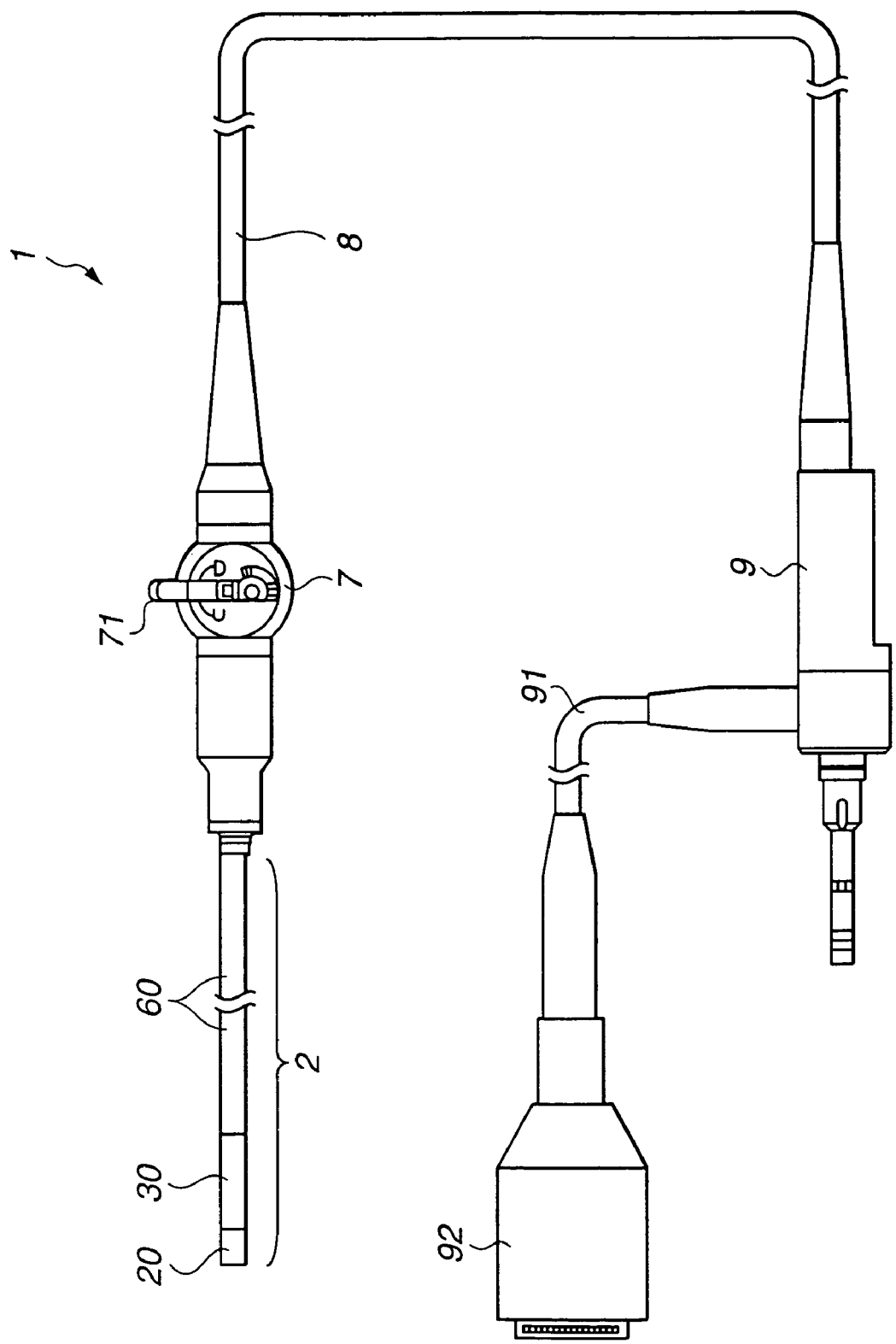
FIG. 1 to FIG. 4 are diagrams for illustrating a first embodiment of the present invention.

As shown in FIG. 1, an endoscope 1 is primarily composed of an insertion portion 2, an operating portion 7, and a universal code 8.

The insertion portion 2 is formed to be slim and elongated, and is inserted into a subject, e.g., the interior of a body cavity. The operating portion 7 is connected to the base end side of the insertion portion 2. This operating portion 7 is formed to have a large diameter in order to double as a grasping section. The universal cord 8 has pliability. This universal cord 8 is extended from the operating portion 7 in a rearward direction.

The insertion portion 2 is composed of a distal end section 20, a bending section 30, and a flexible tube section 60 sequentially connected in that order from the front end side.

The distal end section 20 is formed of a hard member, and an objective optical system and the like are provided in the front end side. The bending section 30 is configured to be brought into an bending operation by operating a bending lever, described below, provided in the operating portion 7. The flexible tube section 60 is configured to have flexibility. A hard tube section may be used as the insertion portion 2 in place of the flexible tube section 60.

The operating portion 7 is provided with the bending lever 71 to remotely bring the bending section 30 into a bending operation. Light guide fibers for transmitting illumination light and signal cables for transmitting various signals are inserted through the universal cord 8 extended from this operating portion 7. This universal cord 8 has an adequate length relative to the insertion portion 2. A light guide connector 9 is provided at the base end portion of this universal cord 8. This light guide connector 9 is detachably attached to a light source device, although not shown in the drawing, which is one of external devices of the endoscope.

A video cable 91 is branched from a side surface of the light guide connector 9. A video connector 92 is provided at the base end portion of the video cable 91. This video connector 92 is detachably and electrically attached to a video processor, although not shown in the drawing, which is a control device or a signal processing device and is one of external devices of the endoscope.

The insertion portion 2 of the endoscope 1 will be described in detail with reference to FIG. 2.

As shown in the drawing, light guide fibers 21 and an image pickup unit 22 are provided in the interior of the insertion portion 2.

The light guide fibers 21 transmit illumination light supplied from the light source device. The image pickup unit 22 photoelectrically converts an observed image into electric signals and transmits them to the video processor.

The distal end section 20 is primarily composed of a main body 23 and a front end tubular member (hereafter abbreviated as a front end member) 24.

The main body 23 is provided with an illumination lens 25, an objective lens 26 constituting the extreme front end part of the image pickup unit 22, and the like. The base end surface of the illumination lens 25 faces the front end surface of the light guide fibers 21. The objective lens 26 of the image pickup unit 22 is provided in the vicinity of the illumination lens 25.

The front end member 24 is disposed by fitting with the main body 23, and is integrally fixed by adhesion.

Each of the surfaces of the main body 23 and the front end member 24 is subjected to, for example, a glass beads treatment, an atmospheric-pressure low-temperature plasma treatment, or a corona discharge treatment, while the surfaces are fitted and adhered to each other.

When the surface is subjected to the glass beads treatment, the surface is provided with small asperities and, thereby, the adhesion is increased. When the surface is subjected to the atmospheric-pressure low-temperature plasma treatment, or the corona discharge treatment, the wettability of the surface is improved and, thereby, the adhesion is increased. The adhesive strength and the watertightness after completion of the autoclave sterilization can be ensured by such an increase in adhesion.

The bending section 30 is provided in the base end side of the distal end section 20. The bending section 30 includes a bending tube 40 composed of sequentially connected plural bending pieces 41, 42, . . . 46. The outer perimeter side of this bending tube 40 is covered with bending rubber 31 made of fluororubber, for example. The thickness dimension of this bending rubber 31 is within the range of 0.2 mm to 0.8 mm, for example.

With respect to the bending tube 40, the bending pieces 41, 42, . . . 46 are freely rotatably connected to one another with rivets 47, and the outer perimeter side of the bending pieces 41, 42, . . . 46 in the state of being sequentially connected is covered with a woven tube (braid) 48. This braid 48 is formed by weaving stainless steel elemental wires or KEVLAR elemental fibers. Both end portions of this woven tube 48 are fixed by soldering, adhesion, or the like to the bending piece 41 and the bending piece 46, respectively, disposed at both ends of the bending tube 40.

With respect to the extreme front end bending piece 41 constituting the bending tube 40, the front end portions of, for example, four bending operation wires 49 are fixed to a fixing part 50 by brazing or soldering. The base ends of the four bending operating wires 49 are fixed to a component operatively associated with the bending lever 71 in the operating portion 7 shown in the FIG. 1 or integrated with the bending lever 71. Therefore, with respect to this endoscope 1, the bending section 30 is bended in, for example, vertical and horizontal directions by a pulling operation of the bending operating wires 49 through the bending lever 71.

Wire holders 51 to control the arrangement locations of the bending operating wires 49 are fixed by brazing or soldering to the inner perimeters of the bending pieces 42, 43, . . . 46 constituting the bending tube 40. The bending operating wires 49 are disposed by being inserted through these wire holders 51.

A joint tube 52 is provided in the base end side of the bending section 30. A coil 53 to guide the bending operating wires 49 is fixed to the inner surface of this joint tube 52. The bending operating wires 49 are inserted through this coil 53.

Figure 2:
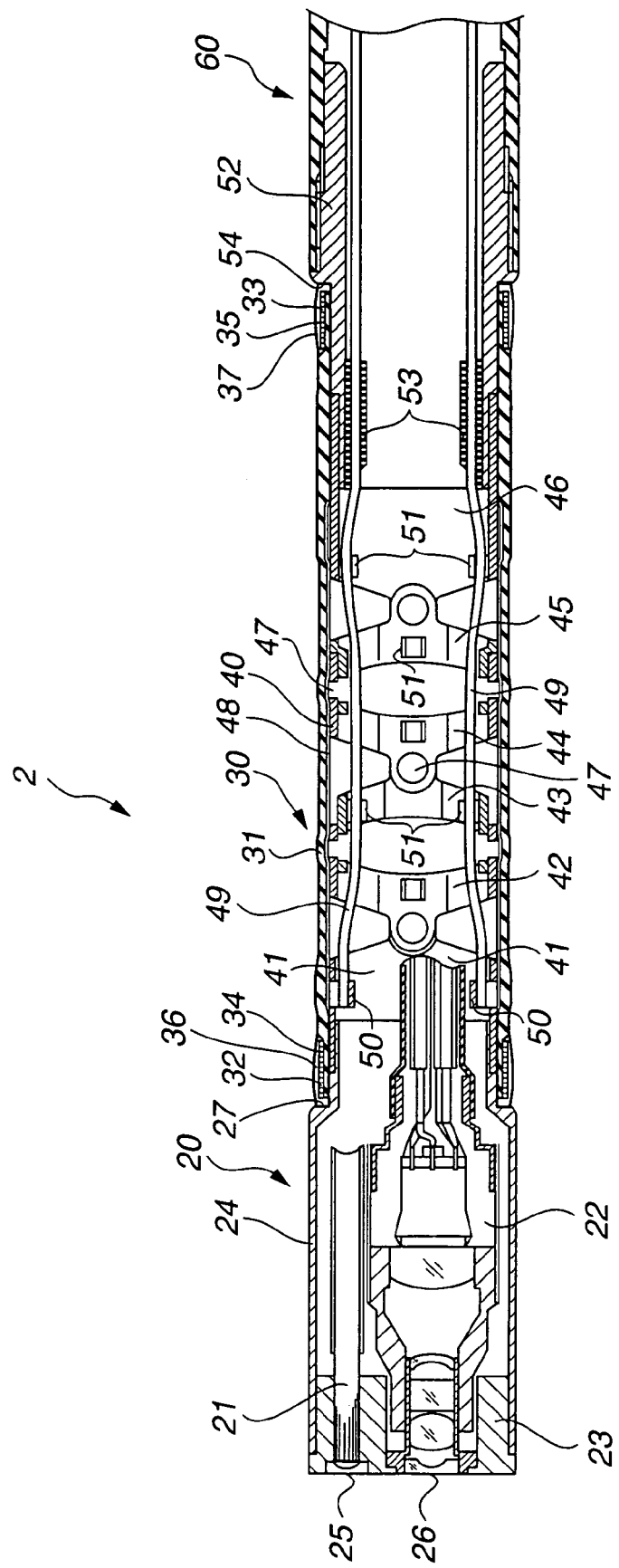
Figure 3:
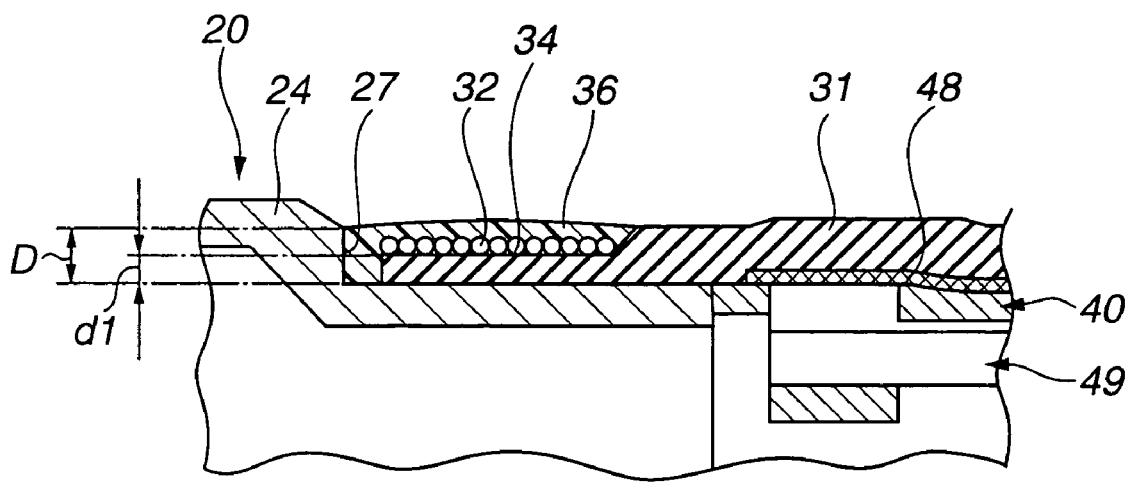
Figure 4:
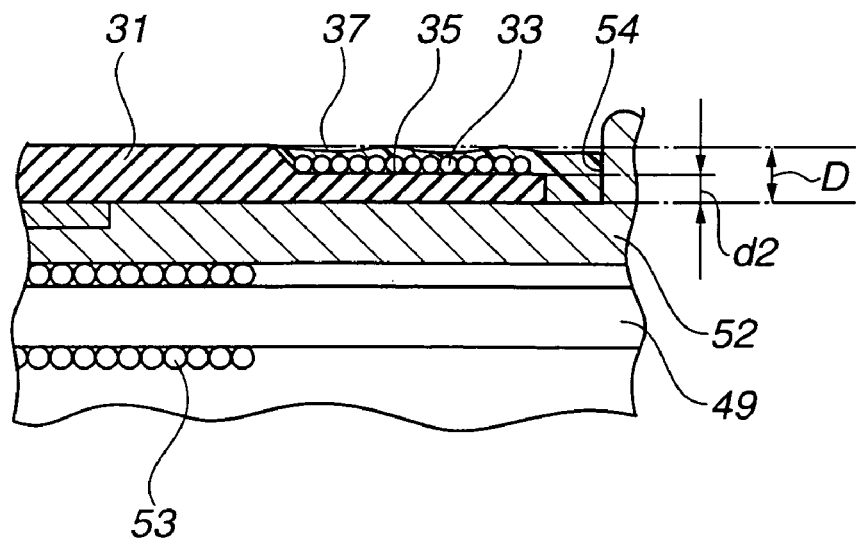

As shown in FIG. 2 to FIG. 4, both end portions of the bending rubber 31 are wrapped with threads 32 and 33, respectively. These threads 32 and 33 crush the bending rubber 31 radially inward. In this manner, the inner perimeter surface of the bending rubber 31 is brought into intimate contact with the outer surfaces of the distal end section 20, the bending tube 40, and the joint tube 52, so as to be fixed watertight. That is, the distal end section 20 is connected to the front end side of the bending tube 40 constituting the insertion portion 2, and the flexible tube section 60 is connected to the base end side of the bending tube 40 through the joint tube 52.

The threads 32 and 33 are, for example, a polybenzazole fiber, a polyphenylene sulfide fiber, an aramid fiber, a silicon carbide-based fiber, a carbon fiber, a silicon fiber, a polyallylate fiber, a ceramic fiber, a titanium fiber, a tungsten fiber, or a polypropylene fiber, or is a union yarn including at least two types of fiber among the above-described fibers.

In the present embodiment, with respect to the thickness dimension d of the portion wrapped with the thread 32 or 33 (hereafter referred to as thread-wrapped portion 34 or 35) of the bending rubber 31, it is assumed that d=d1 or d=d2. This thickness dimension d is controlled at within the range of 40 percent to 95 percent of the thickness dimension D of the bending rubber 31 in the natural state. Consequently, the amount of force in the winding of the threads 32 and 33 are controlled in order to achieve this thickness dimension d.

That is, in the endoscope 1, the thicknesses d=d1 and d=d2 of the bending rubber 31 fastened and fixed by the threads 32 and 33 are controlled at within the range of $0.4D \leq d \leq 0.95D$ relative to the thickness D of the bending rubber 31 in the natural state.

The end portions of the thread-wrapped portions 34 and 35 are provided in the locations at a distance of, for example, one to two times the outer diameters of the threads 32 and 33 from the end portions of the bending rubber 31.

The end portions of the bending rubber 31 are provided in the locations having spacings of, for example, 2 to 3 mm from the height difference portion end surface 27 of the distal end section 20 and the height difference portion end surface 54 of the joint tube 52, respectively.

The threads 32 and 33 of the thread-wrapped portions 34 and 35 are fixed by adhesion with adhesives 36 and 37. When these adhesives 36 and 37 are cured, the curing may be carried out in an atmosphere at, for example, 110 degrees to 140 degrees which is the same temperature as, for example, the sterilization temperature during autoclaving.

(Operation)

The endoscope 1 configured as described above was put in an autoclave apparatus, and it was checked whether the watertightness of both end portions of the bending rubber 31 was broken.

With respect to the conditions during the autoclave sterilization at this time, the temperature in the sterilization step is controlled at 135° C., and the time of the sterilization step is controlled at 5 minutes. The material of the bending rubber 31, the thickness of the bending rubber 31, the thickness of the bending rubber 31 wrapped with the thread, the ratio of the thickness of the bending rubber 31 at the thread-wrapped portion 34 or 35 to the thickness of the bending rubber 31 in the natural state, the material of the thread, and the outer diameter of the tread are as shown in Table 1.

endoscope is put in an autoclave apparatus, entrance of large amount of high-temperature and high-pressure steam into the interior of the endoscope is prevented.

In these manners, components in the interior of the endoscope can be prevented from being deteriorated due to high-temperature and high-pressure steam during autoclave sterilization.

As described above, in the first embodiment, since the thickness dimensions of the thread-wrapped portions 34 and 35 of the bending rubber 31 are controlled at 40 percent or more of the thickness dimension of the bending rubber in the natural state, the bending rubber 31 is not excessively fastened by the threads 32 and 33. That is, the pressures applied to the bending rubber 31 by the threads 32 and 33 are prevented from becoming excessively large.

TABLE 1

| MATERIAL OF BENDING RUBBER | FLUORO-RUBBER | FLUORO-RUBBER | FLUORO-RUBBER | FLUORO-RUBBER | FLUORO-RUBBER |
|---|---|---|---|---|---|
| THICKNESS OF BENDING RUBBER | 0.5 mm | 0.5 mm | 0.5 mm | 0.5 mm | 0.5 mm |
| THICKNESS OF BENDING RUBBER AT THREAD-WRAPPED PART | 0.15 mm | 0.20 mm | 0.25 mm | 0.475 mm | 0.5 mm (NO THREAD-WRAPPED PART) |
| RATIO OF THICKNESS OF BENDING RUBBER AT THREAD-WRAPPED PART TO THICKNESS OF BENDING RUBBER IN NATURAL STATE | 30% | 40% | 50% | 95% | 100% |
| MATERIAL OF THREAD | POLY-ALLYLATE-FIBER | POLY-ALLYLATE-FIBER | POLY-ALLYLATE-FIBER | POLY-ALLYLATE-FIBER | — |
| OUTER DIAMETER OF THREAD | 0.15 mm | 0.15 mm | 0.15 mm | 0.15 mm | — |
| OCCURRENCE OF BREAK OF BENDING RUBBER AFTER AUTOCLAVING | OCCURRED | NONE | NONE | NONE | NONE |
| OCCURRENCE OF BREAK OF WATERTIGHTNESS AFTER AUTOCLAVING | OCCURRED | NONE | NONE | NONE | WATERTIGHTNESS WAS BROKEN IN EARLY STAGE |

Occurrence of break of watertightness after 100 times of treatments in an autoclave apparatus is shown in Table 1. As is clear from Table 1, when the ratio of the thickness of the bending rubber 31 at the thread-wrapped portion to the thickness of the bending rubber 31 in the natural state is 40 percent to 95 percent, break of the watertightness does not occur. However, when the ratio of the thickness of the bending rubber 31 at the thread-wrapped portion to the thickness of the bending rubber 31 in the natural state was out of the range of 40 percent to 95 percent, the watertightness was not ensured.

The occurrence of break of watertightness was checked and determined by presence or absence of air leakage when the internal pressure of the endoscope 1 was controlled at $4.9 \times 10^4$ Pa.

The thicknesses of the bending rubber 31 at the thread-wrapped portions 34 and 35 are controlled at within the range of 40 percent to 95 percent of the thickness of this bending rubber 31 in the natural state, while the bending rubber 31 covers the bending tube 40, and thereby, the bending rubber 31 is prevented from interfering the bending operation of the bending section. In addition, entrance of water into the interior of the endoscope is prevented. Furthermore, when the In the first embodiment, since the thickness dimension of the bending rubber 31 is controlled at 95 percent or less of the thickness dimension of the bending rubber in the natural state, when the bending rubber 31 is crushed radially inward and the inner perimeter of this bending rubber 31 is brought into intimate contact with the outer surfaces of the distal end section 20, bending tube 40, and the joint tube 52 so as to be fixed while the watertightness is ensured, the threads 32 and 33 are prevented from shifting in the longitudinal direction.

Furthermore, since the threads 32 and 33 are formed from any one of a polybenzazole fiber, a polyphenylene sulfide fiber, an aramid fiber, a silicon carbide-based fiber, a carbon fiber, a silicon fiber, a polyallylate fiber, a ceramic fiber, a titanium fiber, a tungsten fiber, a polypropylene fiber, and a union yarn including at least two types of fiber among the above-described fibers, the amount of shrinkage of the threads 32 and 33 themselves due to high-temperature and high-pressure steam during autoclave sterilization are small and, in addition, the threads 32 and 33 themselves are not deteriorated.

EFFECTS

As described above, according to the first embodiment, since the bending rubber 31 is prevented from being excessively strong fastened by the threads 32 and 33, the bending rubber 31 can be reliably prevented from being broken due to softening during the autoclave sterilization.

According to the first embodiment, since the amount of shrinkage of the threads 32 and 33 are small during the autoclave sterilization, the bending rubber 31 can be prevented from being broken.

Furthermore, according to the first embodiment, the watertightness can be prevented from being broken due to deterioration of the threads 32 and 33.

In these manners, when the endoscope is subjected to autoclave sterilization, the bending rubber of the bending section and the fixing portion of the bending rubber are reliably prevented from being broken, the watertightness is reliably ensured and, thereby, the autoclave sterilization-compatible endoscope 1 can be provided. Therefore, the cost required for the endoscope inspection can be reduced and, in addition, the workability can be improved.

Both end portions of the bending rubber 31 may be wrapped with a tape made of, for example, a thermosetting resin, a thermoplastic resin, or an elastomer instead of the wrapping with the threads 32 and 33 and, thereby, both end portions of the bending rubber 31 may be fixed watertight.

Figure 5:
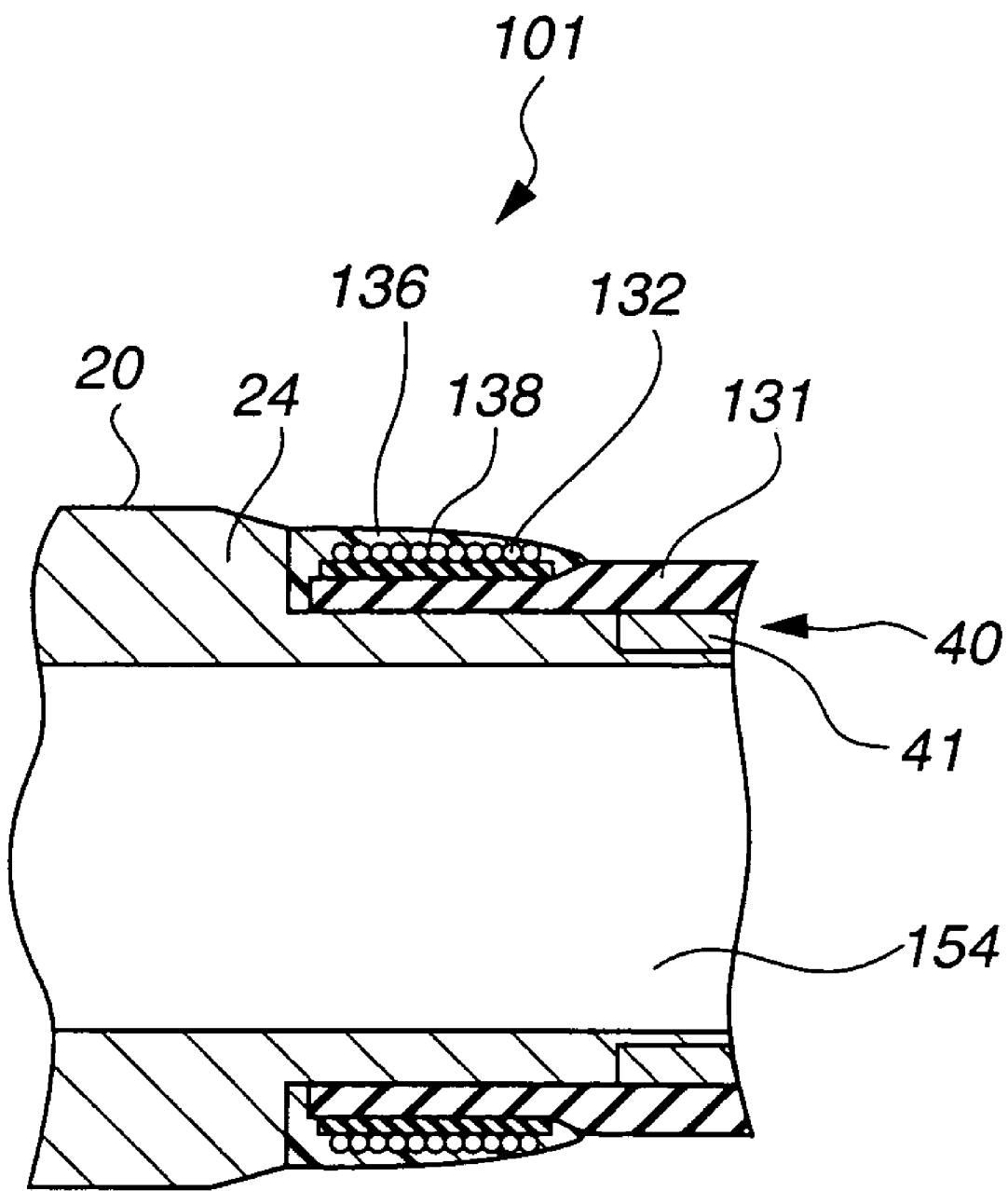
FIG. 5 is a sectional view showing the junction between the front end side of a bending section and a front end cover of an endoscope according to a second embodiment of the present invention.

The second embodiment of the present invention will be described with reference to FIG. 5.

In the description of this second embodiment, constituent elements similar to those in the first embodiment are indicated by the same reference numerals as in the first embodiment, and detailed explanations will not be provided. Constituent elements not shown in FIG. 5 will be described with reference to FIG. 2 in place of FIG. 5.

(Construction)

As shown in the drawing, with respect to an endoscope 101 in the second embodiment, the following construction is different from that of the endoscope 1 in the first embodiment.

Cushioning member 138 in the shape of, for example, a pipe are disposed on the outer surfaces of both end portions of the bending rubber 131. A thread 132 is wound around the outer surface of this cushioning member 138. This thread 132 crushes the bending rubber 131 radially inward through the cushioning member 138. The cushioning member 138 and the thread 132 are fixed by adhesion with an adhesive 136.

In this manner, the inner perimeter surface of the bending rubber 131 becomes in the state of intimate contact with the outer surfaces of internal structures 154, e.g., the distal end section 20, bending tube 40, and the joint tube 52 shown in FIG. 2, so as to be fixed watertight.

In the above-described endoscope 101, the winding is carried out with a predetermined amount of force in order that the thickness dimension of the bending rubber 131 at the portion wrapped with the thread 132 becomes 40 percent to 95 percent of the thickness dimension of the bending rubber 131 in the natural state.

The cushioning member 138 is composed of any one of a thin pipe-shaped member, a C ring-shaped member which is the pipe-shaped member with at least a part thereof being separated, and a tape. The cushioning member 138 is composed of any one member of, for example, a metal member, a metal member with a glass coating, a thermosetting resin member, a thermoplastic resin member, a rubber member, and an elastomer.

(Operation)

In the second embodiment, besides the operation in the first embodiment, since the thread 132 is wound from the outer surface side of the cushioning member 138, the bending rubber 131 can be crushed radially inward with uniformity in the longitudinal direction compared with that in the case where the thread is directly wound around the bending rubber.

EFFECTS

As described above, according to the second embodiment, besides the effects in the first embodiment, since the bending rubber 131 can be crushed radially inward with uniformity in the longitudinal direction, the watertightness can be further improved.

Since the pressure (the amount of force) applied to the bending rubber 131 is uniformed, the bending rubber 131 is prevented from being broken at a portion subjected to a large pressure due to variations in the pressure applied to the bending rubber 131.

The third embodiment of the present invention will be described with reference to FIG. 6 to FIG. 8.

In the description of this third embodiment as well, constituent elements similar to those in the first embodiment are indicated by the same reference numerals as in the first embodiment, and detailed explanations will not be provided.

(Construction)

Figure 6:
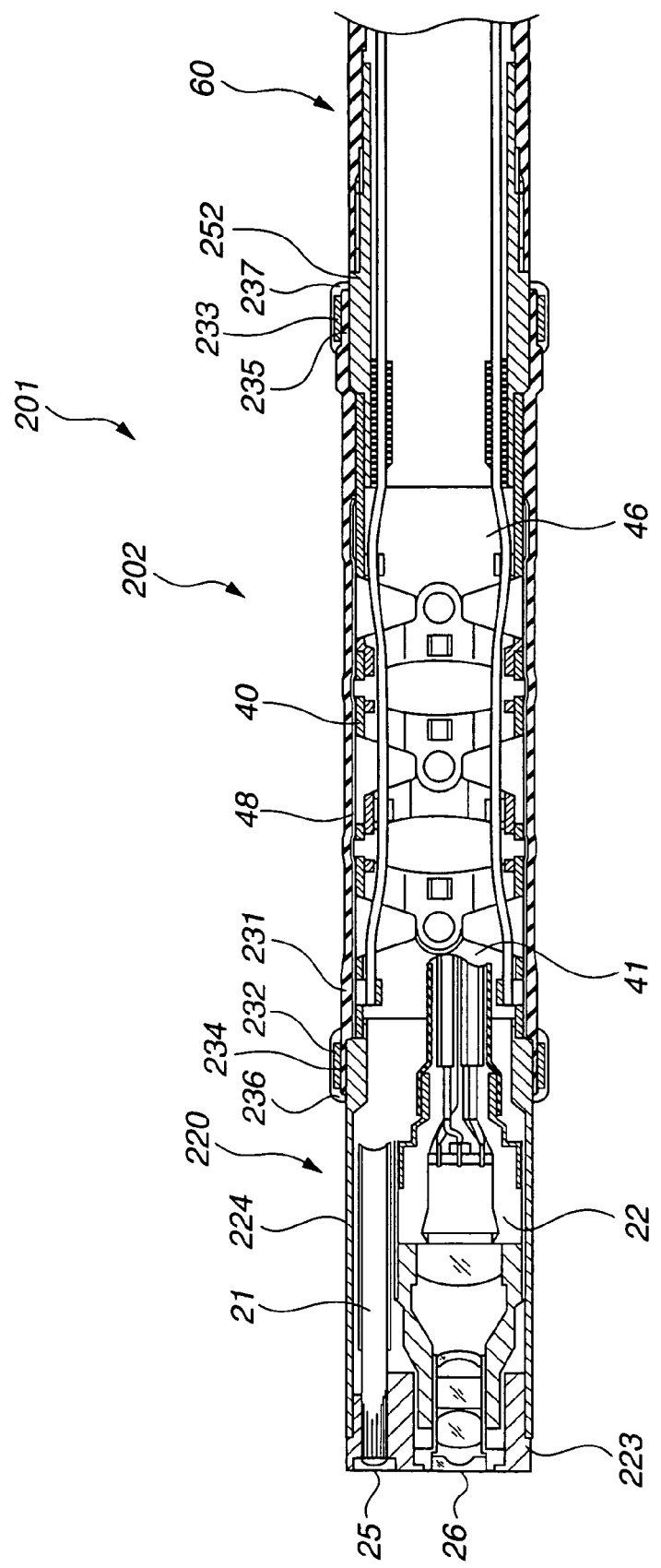
FIG. 6 to FIG. 8 are diagrams for illustrating a third embodiment of the present invention.

As shown in FIG. 6, a distal end section 220 of an insertion portion 202 of an endoscope 201 is composed of a main body 223 and a front end cover 224. The outer diameter dimension of the distal end section 220 from the front end side to the portion covered with a bending rubber 231 is controlled to be larger than the inner diameter dimension of the bending rubber 231 in the natural state, and is controlled to be smaller than the outer diameter dimension of the bending rubber 231 in the natural state.

The outer diameter of the portion covered with the bending rubber 231 of the joint tube 252 constituting the insertion portion 202 is controlled to be larger than the inner diameter dimension of the bending rubber 231 in the natural state, and is controlled to be smaller than the outer diameter dimension of the bending rubber 231 in the natural state.

Figure 7:
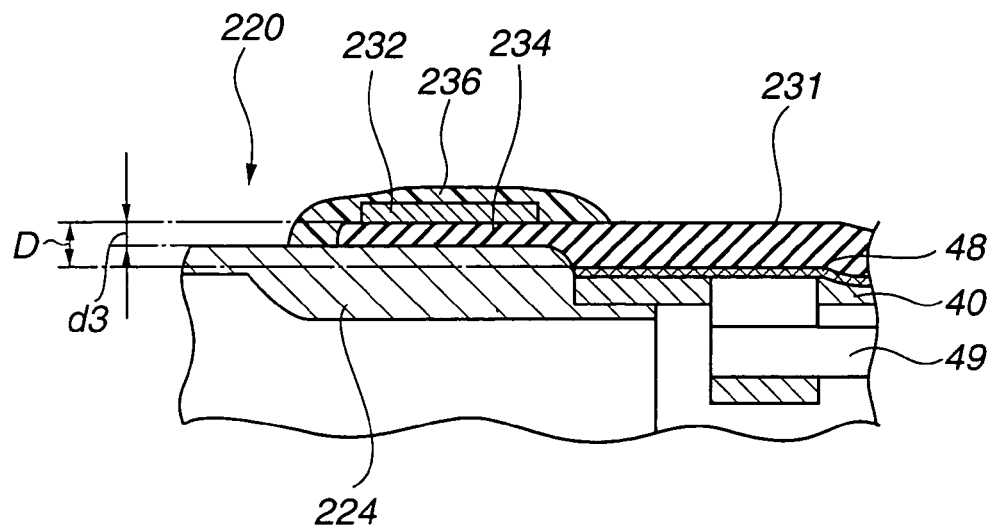
Figure 8:
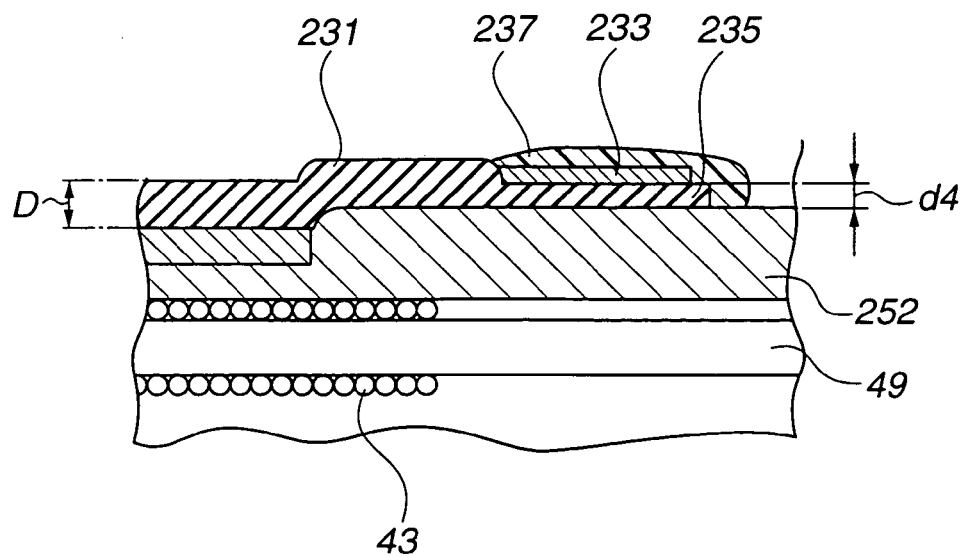

As shown in FIG. 6 to FIG. 8, outer surface sides of both end portions of the bending rubber 231 are provided with pipe-shaped fixing pipes 232 and 233, respectively, serving as the fixing means. The inner diameter dimensions of these fixing pipes 232 and 233 are controlled to be smaller than the outer diameter dimension of the bending rubber 231. Consequently, the fixing pipes 232 and 233 crush the bending rubber 231 radially inward. In this manner, the inner perimeter surface of the bending rubber 231 is brought into intimate contact with the outer surfaces of the distal end section 220, the bending tube 40, and the joint tube 252, so as to achieve the state of being fixed watertight. These fixing pipes 232 and 233 are fixed by adhesion with adhesives 236 and 237 to the covered portions 234 and 235 of the bending rubber 231.

At this time, the thicknesses d=d3 and d=d4 of the covered portions 234 and 235 of the bending rubber 231, covered with the fixing pipes 232 and 233 are controlled at 40 percent to 95 percent of the thickness D of the bending rubber 231 in the natural state.

Each of the fixing pipes 232 and 233 is a member, for example, a metal member, a metal member with a glass coating, a thermosetting resin member, a thermoplastic resin member, a rubber member, or an elastomer.

In the third embodiment, with respect to the operation of disposition of the fixing pipes 232 and 233 on the outer surface of the bending rubber 231, the bending rubber 231 is brought into the state of being pulled in the longitudinal direction, these fixing pipes 232 and 233 are brought into the state of covering the end portions of the bending rubber 231 and, thereafter, the pulling of the bending rubber 231 is terminated. In this manner, the fixing pipes 232 and 233 are disposed in predetermined locations on the bending rubber 231.

In order to inhibit the stretching of the portion of this bending rubber 231 other than the portions to be covered with the fixing pipes 232 and 233 when the bending rubber 231 is pulled, the outer surface of the bending rubber 231 is wrapped with a thick adhesive tape in advance.

With respect to the operation of the attachment of the fixing pipes 232 and 233 on the outer surface of the bending rubber 231, for example, the fixing pipes 232 and 233 may be disposed in predetermined locations on this bending rubber 231, and under this condition, the fixing pipes 232 and 233 may be crushed radially inward.

(Operation)

The endoscope 201 configured as described above was put in an autoclave apparatus, and it was checked whether the watertightness of both end portions of the bending rubber 231 was broken.

With respect to the conditions during the autoclave sterilization at this time, the temperature in the sterilization step is controlled at 135° C., and the time of the sterilization step is controlled at 5 minutes. The material of the bending rubber 231, the thickness of the bending rubber 231, the thickness of the bending rubber 231 at the portion covered with the fixing pipe 232 or 233, the ratio of the thickness of the bending rubber 231 at the portion covered with the fixing pipe 232 or 233 to the thickness of the bending rubber 231 in the natural state, and the material of the fixing pipes 232 and 233 are as shown in Table 2.

watertightness does not occur. However, when the ratios of the thickness of the bending rubber 231 at the portions covered with the fixing pipe 232 and 233 to the thickness of the bending rubber 231 in the natural state were out of the range of 40 percent to 90 percent, the watertightness was not ensured.

The occurrence of break of watertightness was checked and determined by presence or absence of air leakage when the internal pressure of the endoscope 201 was controlled at $4.9 \times 10^4$ Pa.

The ratios of the thickness of the bending rubber 231 at the portion covered with the fixing pipe 232 and 233 to the thickness of the bending rubber 231 in the natural state are controlled at 40 percent to 90 percent and, thereby, the bending rubber 231 is prevented from interfering the bending operation of the bending section. In addition, entrance of water into the interior of the endoscope is prevented. Furthermore, when the endoscope is put in an autoclave apparatus, entrance of large amount of high-temperature and high-pressure steam into the interior of the endoscope is prevented.

In these manners, components in the interior of the endoscope can be prevented from being deteriorated due to the high-temperature, high-temperature, and high-pressure steam during autoclave sterilization.

Each of the fixing pipes 232 and 233 serving as a fixing means may be a C ring-shaped pipe formed by separating at least a part of the shape of a thin pipe.

Fixing means similar to the fixing pipes 232 and 233 include a method in which the surface of the bending rubber

TABLE 2

| MATERIAL OF BENDING RUBBER | FLUORO-RUBBER | FLUORO-RUBBER | FLUORO-RUBBER | FLUORO-RUBBER | FLUORO-RUBBER |
|---|---|---|---|---|---|
| THICKNESS OF BENDING RUBBER | 0.5 mm | 0.5 mm | 0.5 mm | 0.5 mm | 0.5 mm |
| THICKNESS OF BENDING RUBBER AT PORTION COVERED WITH FIXING PIPE | 0.15 mm | 0.20 mm | 0.25 mm | 0.45 mm | 0.5 mm (NO RING) |
| RATIO OF THICKNESS OF BENDING RUBBER AT PORTION COVERED WITH FIXING PIPE TO THICKNESS OF BENDING RUBBER IN NATURAL STATE | 30% | 40% | 50% | 90% | 100% |
| MATERIAL OF RING | SUS304 | SUS304 | SUS304 | SUS304 | — |
| OCCURRENCE OF BREAK OF BENDING RUBBER AFTER AUTOCLAVING | OCCURRED | NONE | NONE | NONE | NONE |
| OCCURRENCE OF BREAK OF WATERTIGHTNESS AFTER AUTOCLAVING | OCCURRED | NONE | NONE | NONE | WATERTIGHTNESS WAS BROKEN IN EARLY STAGE |

Occurrence of break of watertightness after 100 times of treatments in an autoclave apparatus is shown in Table 2. As is clear from Table 2, when the ratios of the thickness of the bending rubber 231 at the portions covered with the fixing pipe 232 and 233 to the thickness of the bending rubber 231 in the natural state are 40 percent to 90 percent, break of the 231 is wrapped with a tape. A member, e.g., a thermosetting resin, a thermoplastic resin, or an elastomer, can be used as the tape at this time.

In this third embodiment, besides the operation in the above-described first embodiment, since the bending rubber 231 is crushed radially inward with the fixing pipes 232 and 233, the bending rubber 231 can be crushed uniformly in the longitudinal direction. Furthermore, the amount of crush of the bending rubber 231 can be precisely and readily controlled by the inner diameter dimension.

EFFECTS

As described above, according to the third embodiment, besides the effects in the first embodiment and the second embodiment, since the bending rubber 231 can be crushed radially inward with precision and uniformity in the longitudinal direction. In this manner, the watertightness can be further improved.

In the third embodiment, since the pressure (the amount of force) applied to the bending rubber 231 is uniformed, the bending rubber 231 is prevented from being broken at a portion subjected to a large pressure due to variations in the pressure applied to the bending rubber 231.

Furthermore, there is an effect of improving workability in assembly.

With respect to the endoscope in the above-described first embodiment, the thickness d of the bending rubber fastened and fixed is controlled at within the range of $0.4D \leq d \leq 0.95D$ relative to the thickness D of the bending rubber in the natural state before being fastened and fixed. However, when the thickness d is within the range of $0.3D < d < 1.0D$ relative to the thickness D, an effect of preventing the bending rubber of the bending section and the bending rubber fixing means from being broken is achieved to at least some extent.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
   a bending section which is provided in a slim and elongated insertion portion to be inserted into a body cavity and which can be bended by a remote control;
   a bending rubber which is disposed on the outer surface of a bending tube including sequentially connected bending pieces constituting the bending section and which constitutes an outer sheath; and
   a fixing means comprising:
      one or more tubular cushioning member disposed on the outer surface of the bending rubber, the one or more tubular cushioning member being configured to crush the bending rubber uniformly with respect to an inner periphery direction in a longitudinal direction, and
      one or more threads wound around the outer surface of the one or more tubular cushioning member,
      wherein the fixing means is configured to control the thicknesses of both end portions of the bending rubber at 40 percent to 95 percent of the thickness of the bending rubber in the natural state and which disposes both end portions of the bending rubber in intimate contact with the bending tube.

2. The endoscope according to claim 1, wherein the fixing means comprises threads disposed on the outer surface of the bending rubber.

3. The endoscope according to claim 2, wherein the thread comprises a polybenzazole fiber, a polyphenylene sulfide fiber, an aramid fiber, a silicon carbide-based fiber, a carbon fiber, a silicon fiber, a polyallylate fiber, a ceramic fiber, a titanium fiber, a tungsten fiber, or polypropylene.

4. The endoscope according to claim 2, wherein the thread is a union yarn comprising at least two threads of a polybenzazole fiber, a polyphenylene sulfide fiber, an aramid fiber, silicon carbide-based fiber, a carbon fiber, a silicon fiber, a polyallylate fiber, a ceramic fiber, a titanium fiber, a tungsten fiber, and polypropylene.

5. The endoscope according to claim 1, wherein the thread comprises a polybenzazole fiber, a polyphenylene sulfide fiber, an aramid fiber, a silicon carbide-based fiber, a carbon fiber, a silicon fiber, a polyallylate fiber, a ceramic fiber, a titanium fiber, a tungsten fiber, or polypropylene.

6. The endoscope according to claim 1, wherein the thread comprises a polybenzazole fiber, a polyphenylene sulfide fiber, an aramid fiber, a silicon carbide-based fiber, a carbon fiber, a silicon fiber, a polyallylate fiber, a ceramic fiber, a titanium fiber, a tungsten fiber, or polypropylene.

7. The endoscope according to claim 1, wherein at least one tubular cushioning member is comprised of a pipe-shaped member.

8. The endoscope according to claim 7, wherein the pipe-shaped member comprises a metal member, a metal member with a glass coating, a thermosetting resin member, a thermoplastic resin member, a rubber member, or an elastomer.

9. The endoscope according to claim 1, wherein at least one tubular cushioning member is comprised of a C ring-shaped pipe which is a thin pipe-shaped member with at least a part thereof being separated.

10. The endoscope according to claim 9, wherein the C ring-shaped pipe comprises a metal member, a metal member with a glass coating, a thermosetting resin member, a thermoplastic resin member, a rubber element, or an elastomer.

11. The endoscope according to claim 1, wherein the fixing means comprises a tape wound around the surface of the bending rubber.

12. The endoscope according to claim 11, wherein the tape comprises a thermosetting resin, a thermoplastic resin, or an elastomer.

13. The endoscope according to claim 1, wherein the thickness of the bending rubber is controlled at within the range of 0.2 mm to 0.8 mm.

* * * * *